(12) United States Patent
Rivers et al.

(10) Patent No.: US 9,480,646 B2
(45) Date of Patent: Nov. 1, 2016

(54) SUSTAINED RELEASE SIRNA FOR OCULAR DRUG DELIVERY

(71) Applicant: Allergan, Inc., Irvine, CA (US)

(72) Inventors: Hongwen M. Rivers, San Diego, CA (US); Lon T. Spada, Walnut, CA (US); Michelle Luu, Anaheim, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 14/608,514

(22) Filed: Jan. 29, 2015

(65) Prior Publication Data

US 2015/0141348 A1 May 21, 2015

Related U.S. Application Data

(63) Continuation of application No. 13/187,117, filed on Jul. 20, 2011, now Pat. No. 8,946,170.

(60) Provisional application No. 61/366,500, filed on Jul. 21, 2010.

(51) Int. Cl.
| | |
|---|---|
| *A61K 47/34* | (2006.01) |
| *A61K 47/48* | (2006.01) |
| *A61K 31/713* | (2006.01) |
| *C12N 15/113* | (2010.01) |
| *A61K 9/00* | (2006.01) |
| *A61K 31/7088* | (2006.01) |
| *A61K 48/00* | (2006.01) |

(52) U.S. Cl.
CPC ......... *A61K 9/0051* (2013.01); *A61K 31/7088* (2013.01); *A61K 31/713* (2013.01); *A61K 47/34* (2013.01); *A61K 47/48046* (2013.01); *A61K 47/48246* (2013.01); *A61K 47/48323* (2013.01); *A61K 48/0075* (2013.01); *C12N 15/113* (2013.01); *C12N 2310/14* (2013.01); *C12N 2310/3513* (2013.01); *C12N 2310/3515* (2013.01)

(58) Field of Classification Search
CPC ........... A61K 31/7088; A61K 31/713; A61K 47/34; A61K 47/48046; A61K 47/48246; A61K 47/48323; A61K 48/0075; A61K 9/0051; C12N 15/113; C12N 2310/14; C12N 2310/3513; C12N 2310/3515
USPC .............................................. 514/20.8, 44 A
See application file for complete search history.

(56) References Cited

U.S. PATENT DOCUMENTS

| | | | |
|---|---|---|---|
| 5,869,079 | A | 2/1999 | Wong et al. |
| 7,700,760 | B2 | 4/2010 | McSwiggen et al. |
| 8,039,010 | B2 | 10/2011 | Trogden et al. |
| 2005/0244467 | A1 | 11/2005 | Nivaggioli et al. |
| 2005/0244469 | A1 | 11/2005 | Whitcup et al. |
| 2005/0281861 | A1 | 12/2005 | Hughes et al. |
| 2006/0040882 | A1 | 2/2006 | Chen et al. |
| 2006/0182783 | A1 | 8/2006 | Hughes et al. |
| 2008/0033351 | A1 | 2/2008 | Trogden et al. |
| 2008/0107694 | A1 | 5/2008 | Trogden et al. |
| 2008/0118500 | A1 | 5/2008 | Liu et al. |
| 2008/0268051 | A1 | 10/2008 | Hughes et al. |
| 2009/0186059 | A1 | 7/2009 | Johnson et al. |
| 2009/0226531 | A1 | 9/2009 | Lyons et al. |
| 2009/0258924 | A1 | 10/2009 | Lyons et al. |
| 2009/0280181 | A1* | 11/2009 | Slager .................. A61K 9/0024 424/484 |
| 2009/0312402 | A1 | 12/2009 | Contag et al. |
| 2010/0310670 | A1 | 12/2010 | Okada et al. |
| 2010/0311808 | A1 | 12/2010 | Lyons et al. |
| 2012/0022137 | A1 | 1/2012 | Rivers et al. |

FOREIGN PATENT DOCUMENTS

| | | |
|---|---|---|
| CA | 2621055 | 3/2007 |
| WO | 2008-134644 | 11/2008 |
| WO | 2010-118213 | 10/2010 |
| WO | 2011-084366 | 7/2011 |

OTHER PUBLICATIONS

Akinc, Akin et al, A Combinatorial Library of Lipid-Like Materials for Delivery of RNAi Therapeutics, Nature Biotechnology, May 2008, 561-569, 26(5).

Auguste, Debra et al, Triggered Release of siRNA From Poly(Ethylene Glycol)-Protected, pH-Dependent Liposomes, Journal of Controlled Release, 2008, 266-274, 130.

Bartel, David, MicroRNAs: Genomics, Biogenesis, Mechanism, and Function, Cell, Jan. 23, 2004, 281-297, 116.

Cao, Haoqing et al, RNA Interference by Nanofiber-Based siRNA Delivery System, Journal of Controlled Release, 2010, 203-212, 144.

Heller, Jorge, Biodegradable Polymers in Controlled Drug Delivery, Critical Reviews in Therapeutic Drug Carrier Systems, 1987, 39-90, 1 (1).

Krebs, Melissa et al, Localized and Sustained Delivery of Silencing RNA From Macroscopic Biopolymer Hydrogels, J. Am. Chem. Soc., 2009, 9204-9206, 131.

Lorenz, Christina et al, Steroid and Lipid Conjugates of siRNAs to Enhance Cellular Uptake and Gene Silencing in Liver Cells, Bioorganic & Medicinal Chemistry Letters, 2004, 4975-4977, 14.

Mahato, Ram et al, Cationic Lipid-Based Gene Delivery Systems: Pharmaceutical Perspectives, Pharmaceutical Research, 1997, 853-859, 14(7).

Meade, Bryan et al, Exogenous siRNA Delivery Using Peptide Transduction Domains/Cell Penetrating Peptides, Advanced Drug Delivery Reviews, 2007, 134-140, 59.

(Continued)

*Primary Examiner* — Julie Ha
(74) *Attorney, Agent, or Firm* — Brigitte C. Phan; Ted A. Chan

(57) ABSTRACT

The present invention provides an ocular implant of siRNA complexed with a transfection agent such as cationic lipids and short cell penetration peptides, wherein the complex is associated with a biocompatible polymer. The biocompatible polymer includes a polymeric matrix configured to release the complex into the eye of a patient at therapeutic levels for a time sufficient to treat an ocular condition or disease.

3 Claims, 1 Drawing Sheet

(56) References Cited

OTHER PUBLICATIONS

Murata, Naoyuki et al, Anti-Tumor Effects of Anti-VEGF siRNA Encapsulated with PLGA Microspheres in Mice, Journal of Controlled Release, 2008, 246-254, 126.

Santel, A. et al, A Novel siRNA-Lipoplex Technology for RNA Interference in the Mouse Vascular Endothelium, Gene Therapy, 2006, 1222-1234, 13.

Schiffelers, Raymond et al, Transporting silence: Design of carriers for siRNA to angiogenic endothelium, Journal of Controlled Release, 2005, 5-14, vol. 109.

Simeoni, Federica et al, Insight into the Mechanism of the Peptide-Based Gene Delivery System MPG: Implications for Delivery of siRNA into Mammalian Cells, Nucleic Acids Research, 2003, 2717-2724, 31(11).

Song, Erwei et al, Antibody mediated in vivo delivery of small interfering RNAs via cell-surface receptors, Nature Biotechnology, Jun. 2005, 709-717, vol. 23, No. 6.

United States Pharmacopeia, The National Formulary, USP23, 1995, 1790-1798, 18.

Vanden-Broucke, Roosmarigin et al, Prolonged Gene Silencing in Hepatoma Cells and Primary Hepatocytes After Small Interfering RNA Delivery With Biodegradable Poly($\beta$-Amino Esters), The Journal of Gene Medicine, 2008, 783-794, 10.

Vidal, Pierre et al, Conformations of a synthetic peptide which facilitates the cellular delivery of nucleic acids, Letters in Peptide Science, 1997, 227-230, 4.

Wolfrum, Christian et al, Mechanisms and optimization of in vivo delivery of lipophilic siRNAs, Nature Biotechnology, Oct. 2007, 1149-1157, vol. 25, No. 10.

Patent Cooperation Treaty, Notification of Transmittal of the International Search Report and the Written Opinion of the International Searching Authority, or the Declaration, Form PCT/ISA/220, Int. App. No. PCT/US2011/044694, Jun. 29, 2012.

* cited by examiner

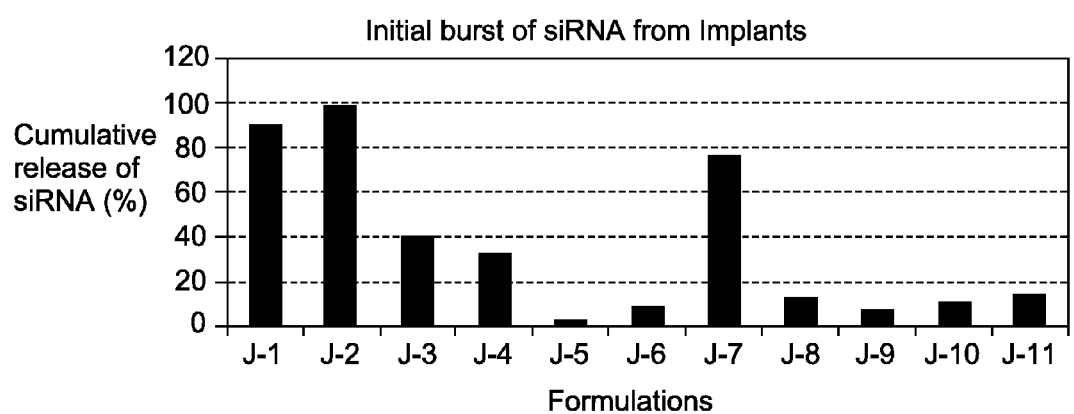

SUSTAINED RELEASE SIRNA FOR OCULAR DRUG DELIVERY

CROSS-REFERENCE TO RELATED APPLICATIONS

This application is a continuation application of U.S. application Ser. No. 13/187,117, filed Jul. 20, 2011, which claims the benefit of U.S. Provisional Application 61/366,500, filed Jul. 21, 2010, which is hereby incorporated by reference in their entirety.

REFERENCE TO A SEQUENCE LISTING

This application includes the following sequence listing, submitted herewith in ASCII text file format: "Rivers et al. 18773 Sequence Listing_ST25.txt", for "Sustained Release siRNA for Ocular Drug Delivery", Ser. No. 13/187,117, containing approximately 1006 bytes, created on Jul. 19, 2011, and hereby incorporated by reference.

BACKGROUND OF THE INVENTION

The present invention relates to ocular implants comprising siRNA complexed with a transfection agent, said complex being associated with a biocompatible polymer configured to release said complex into the eye of a patient at therapeutic levels for a time sufficient to treat an ocular condition or disease.

Small interfering RNA (siRNA), sometimes known as short interfering RNA or silencing RNA, is a class of double-stranded RNA molecules, 20-25 nucleotides (nt) in length, that play a variety of roles in biology. siRNA is involved in the RNA interference (RNAi) pathway, where it interferes with the expression of a specific gene.

Synthetic siRNAs have been shown to be able to induce RNAi in mammalian cells. This discovery has led to a surge in interest in harnessing RNAi for biomedical research and drug development.

siRNAs have a well-defined structure: a short (usually 21-nt) double strand of RNA (dsRNA) with 2-nt 3' overhangs on either end: Each strand has a 5' phosphate group and a 3' hydroxyl (—OH) group. This structure is the result of processing by Dicer, an enzyme that converts either long dsRNAs or small hairpin RNAs into siRNAs. siRNAs can also be exogenously (artificially) introduced into cells by various transfection methods to bring about the specific knockdown of a gene of interest. Essentially, any gene of which the sequence is known can thus be targeted based on sequence complementarily with an appropriately tailored siRNA. This has made siRNAs an important tool for gene function and drug target validation studies in the post-genomic era.

Transfection of an exogenous siRNA can be problematic because the gene knockdown effect is only transient, particularly in rapidly dividing cells. One way of overcoming this challenge is to modify the siRNA in such a way as to allow it to be expressed by an appropriate vector, e.g., a plasmid. This is done by the introduction of a loop between the two strands, thus producing a single transcript, which can be processed into a functional siRNA. Such transcription cassettes typically use an RNA polymerase III promoter (e.g., U6 or H1), which usually directs the transcription of small nuclear RNAs (snRNAs) (U6 is involved in gene splicing; H1 is the RNase component of human RNase P). It is assumed (although not known for certain) that the resulting siRNA transcript is then processed by Dicer.

It has been found that dsRNA can also activate gene expression, a mechanism that has been termed "small RNA-induced gene activation" or RNAa. It has been shown that dsRNAs targeting gene promoters induce potent transcriptional activation of associated genes. RNAa was demonstrated in human cells using synthetic dsRNAs, termed "small activating RNAs" (saRNAs).

Given the ability to knock down essentially any gene of interest, RNAi via siRNAs has generated a great deal of interest in both basic and applied biology. There are an increasing number of large-scale RNAi screens that are designed to identify the important genes in various biological pathways. Because disease processes also depend on the activity of multiple genes, it is expected that in some situations turning off the activity of a gene with an siRNA will produce a therapeutic benefit.

Results of therapeutic RNAi trials indicated for age-related macular degeneration, (ARMD) demonstrated that siRNAs are well tolerated and have suitable pharmacokinetic properties. siRNAs and related RNAi induction methods therefore stand to become an important new class of drugs in the foreseeable future.

Despite the potential benefits of developing drugs based on siRNAs, positively charged and highly water soluble siRNAs are known to be unable to penetrate though cell membranes to reach their intracellular specific gene targets and thus have very low bioavailability.

BRIEF SUMMARY OF THE INVENTION

The present invention provides an ocular implant comprising siRNA complexed with a transfection agent selected from the group consisting of cationic lipids and short cell penetration peptides, wherein said complex is associated with a biocompatible polymer, e.g. a polymeric matrix, configured to release said complex into the eye of a patient at therapeutic levels for a time sufficient to treat an ocular condition or disease.

The present invention is also directed to an ocular implant comprising a microRNA (miRNA) complexed with a transfection agent selected from the group consisting of cationic lipids and short cell penetration peptides, wherein said complex is associated with a biocompatible polymer, e.g. a polymeric matrix, configured to release said complex into the eye of a patient at therapeutic levels for a time sufficient to treat an ocular condition or disease. The miRNA may single stranded RNA with no base-pairing, or double stranded RNA, comprising separate non-covalently linked strands held together by base pairing only, or consisting of a single strand that folds back on itself to form a hairpin loop.

miRNAs are naturally occurring short (~22 nucleotide) RNAs found in many plant and animal cells that may inhibit protein production by promoting cleavage of the corresponding mRNA or by blocking its translation into protein. For a review, see for example, Bartel et al. (2004) Cell 116:281-297.

An implant of the present invention may be placed, inserted, injected, or implanted into an ocular region of an eye in an individual affected with an ocular disease or condition to treat one or more symptoms of the disease or condition and/or to improve the visual performance of the eye in an individual.

BRIEF DESCRIPTION OF THE DRAWINGS

FIG. 1 shows the amount of siRNA released from various implants after one day in release medium under sink conditions. The formulation number of each implant is given on the x-axis. The composition of each formulation is given in Tables 3 and 4. The amount of siRNA released from each implant is expressed as a percentage of the amount of siRNA initially present in the implant.

DETAILED DESCRIPTION OF THE INVENTION

An ocular implant, characterized as having increased bioavailability of siRNA, comprises siRNA complexed with a transfection agent selected from the group consisting of cationic lipids and cell penetration peptides, having from 5 to 40 amino acids, said complex being associated with a biocompatible polymer, e.g. a polymeric matrix, configured to release said complex into the eye of a patient at therapeutic levels for a time sufficient to treat an ocular condition or disease. In the process and compositions of this invention, short peptides or cationic lipids, collectively referred to as transfection agents, with cell membrane penetration properties are allowed to form complexes with siRNA molecules and the complex is incorporated into biodegradable PLGA implants. Notwithstanding the high water solubility of siRNAs which makes it difficult to produce highly loaded implants necessary for a sustained duration of action, the resulting implants can have a higher loading making it possible to achieve a longer-duration sustained release of the siRNA, and the released siRNA complex can be taken up by the cells.

Many short peptide sequences (3-50 or 5-40 amino acids) have been discovered that are permeable to mammalian cells. It has now been found that these cell penetrating peptides have the capacity to deliver siRNAs into the cell's interior through either endocytosis or a direct penetration through cell membranes. In endocytosis, the extracellular molecules internalized through lipid vesicles called endosomes have to avoid being degraded or damaged by the acidic environment inside the endosome in order to escape into the cytosol and exhibit their biological function. In the direct cell penetration mechanism, the peptides can initiate cell membrane changes that allow them to enter cells along with their complexed siRNA independent of the endosomal pathway. The direct cell mechanism provides a more direct and advantageous drug delivery route.

In addition, short peptides are more likely to display good thermal stability and are less prone to degradation or aggregation than complex protein or peptide molecules, making them suitable for use in hot-melt extruded implants.

siRNAs are well known in the art and may be identified in accordance with procedures disclosed in various publications, including, for example, U.S. Pat. No. 7,700,760, which is hereby incorporated by reference in its entirety. Thus, the siRNA utilized in the compositions and methods of this invention are those effective to treat diseases and conditions of the eye, i.e. ophthalmic diseases and conditions.

As discussed above, the ocular implant of the invention comprises siRNA complexed with a transfection agent selected from the group consisting of cationic lipids and cell penetration peptides. (Throughout this specification, as related to the compositions of the present invention, it is understood that siRNA is in the form of a complex with the above transfection agent, even if the term does not include the complete description but only states the term "siRNA".)

Short peptides that are able to form stable non-covalent complexes with siRNA and penetrate the cell membrane through nonendocytic uptake and which may be used in the instant invention include: Polylysines and Polyarginines. In one embodiment, the polyarginine peptide consists of nine contiguous arginines (R9). Pep-1 (KETWWETWWTEWS-QPKKKRKV [SEQ ID NO:1]); and MPG, derived from the fusion peptide domain of HIV-1 gp41 protein and the nuclear localization signal of SV40 large T antigen, modified for delivery into cytoplasm rather than nucleus (GAL-FLGFLGAAGSTMGAWSQPKSKRKV [SEQ ID NO:2]).

Alternatively, in the complexes of this invention, cationic lipids may be used to bind and condense negatively charged siRNAs. They can also interact with cell membranes via their hydrophobic lipid anchor groups and help deliver siRNA into cells.

In other embodiments, the following are examples of cationic lipids that can be used to form the siRNA complexes that are used in the implants of this invention: Cetyl trimethylammonium bromide (hexadecyl trimethyl ammonium bromide, and other alkyltrimethylammonium salts); Cetylpyridinium chloride; Polyethoxylated tallow amine; Benzalkonium chloride; and Benzethonium chloride.

In one embodiment, complexes that are used in the implants of this invention are prepared as follows:

Short peptides can be dissolved in water and mixed with siRNA in aqueous solution and then lyophilized into a dry powder. The dry powder of peptides and siRNA can then be further blended with the polymer, e.g. a polylactide or a polylactide-co-glycolide acid copolymer (PLA/PLGA polymer), and compacted into pellets, or hot melt extruded into solid implants.

Cationic lipids can be first dissolved in ethanol before they are mixed with an aqueous siRNA solution, and then the complete solution is lyophilized into a dry powder. The dry powder of peptides and siRNA can then be further blended with a polymer, e.g. a polylactic acid (PLA) and/or polylactic acid polyglycolic acid (PLGA) copolymer, and compacted into pellets, or hot melt extruded into solid implants.

In one embodiment, the complex is formed into an implant by associating it with a polymer that is compatible with the body of the patient, e.g. an ocular implant will comprise a polymer that is compatible with the environment of the eye of the patient being treated by the implantation of the implant of this invention.

Suitable polymeric materials or compositions for use in the implant include those materials, which are compatible, i.e. biocompatible, with the eye so as to cause no substantial interference with the functioning or physiology of the eye. Such materials preferably are at least partially and more preferably substantially completely biodegradable or bioerodible.

Examples of useful polymeric materials include, without limitation, such materials derived from and/or including organic esters and organic ethers, which when degraded result in physiologically acceptable degradation products, including the monomers. Also, polymeric materials derived from and/or including, anhydrides, amides, orthoesters and the like, by themselves or in combination with other monomers, may also find use. The polymeric materials may be addition or condensation polymers, advantageously condensation polymers. The polymeric materials may be cross-linked or non-cross-linked, for example not more than lightly cross-linked, such as less than about 5%, or less than about 1% of the polymeric material being cross-linked. For the most part, besides carbon and hydrogen, the polymers will include at least one of oxygen and nitrogen, advantageously oxygen. The oxygen may be present as oxy, e.g. hydroxy or ether, carbonyl, e.g. non-oxo-carbonyl, such as carboxylic acid ester, and the like. The nitrogen may be present as amide, cyano and amino. The polymers set forth in Heller, Biodegradable Polymers in Controlled Drug Delivery, In: CRC Critical Reviews in Therapeutic Drug Carrier Systems, Vol. 1, CRC Press, Boca Raton, Fla. 1987, pp 39-90, which describes encapsulation for controlled drug delivery, may find use in the present implants.

Of additional interest are polymers of hydroxyaliphatic carboxylic acids, either homopolymers or copolymers, and polysaccharides. Polyesters of interest include polymers of D-lactic acid, L-lactic acid, racemic lactic acid, glycolic acid, polycaprolactone, and combinations thereof. Generally, by employing the L-lactate or D-lactate, a slowly eroding polymer or polymeric material is achieved, while erosion is substantially enhanced with the lactate racemate.

Among the useful polysaccharides are, without limitation, calcium alginate, and functionalized celluloses, particularly carboxymethylcellulose esters characterized by being water insoluble, a molecular weight of about 5 kD to 500 kD, for example.

Other polymers of interest include, without limitation, polyvinyl alcohol, polyesters, polyethers and combinations thereof, which are biocompatible and may be biodegradable and/or bioerodible.

Some preferred characteristics of the polymers or polymeric materials for use in the present invention may include biocompatibility, compatibility with the siRNA and/or the siRNA complex, ease of use of the polymer in making the implant of the present invention, a half-life in the physiological environment of at least about 6 hours, preferably greater than about one day, and not significantly increasing the viscosity of the vitreous.

The biodegradable polymeric materials, which are included to form the matrix are desirably subject to enzymatic or hydrolytic instability. Water-soluble polymers may be cross-linked with hydrolytic or biodegradable unstable cross-links to provide useful water insoluble polymers. The degree of stability can be varied widely, depending upon the choice of monomer, whether a homopolymer or copolymer is employed, employing mixtures of polymers, and whether the polymer includes terminal acid groups.

Equally important to controlling the biodegradation of the polymer and hence the extended release profile of the implant is the relative average molecular weight of the polymeric composition employed in the implant. Different molecular weights of the same or different polymeric compositions may be included in the implant to modulate the release profile. In certain implants, the relative average molecular weight of the polymer will range from about 9 to about 250 kD, preferable from about 10 to about 100 kD, and more preferable from about 12 to about 45 kD.

In some implants, copolymers of glycolic acid and lactic acid are used, where the rate of biodegradation is controlled by, among other things, factors such as the lactide to glycolide ratio, the molecular weight, and the polymer chain end groups. An example of such a copolymer is a polylactic acid polyglycolic acid copolymer, also referred to as a poly(lactide-co-glycolide) or PLGA. The most rapidly degraded copolymer has roughly equal amounts of glycolic acid and lactic acid. Homopolymers, or copolymers having ratios other than equal, are more resistant to degradation. The ratio of glycolic acid to lactic acid will also affect the brittleness of the implant, where a more flexible implant is desirable for larger geometries. The percentage (%) of polylactic acid in the polylactic acid polyglycolic acid (PLGA) copolymer can be 0-100%, preferably about 15-85%, more preferably about 35-65%. In some implants, a 50/50 PLGA copolymer is used.

The biodegradable polymer matrix of the ocular implant may comprise a mixture of two or more biodegradable polymers. The first biodegradable polymer may be a poly (D,L-lactide-co-glycolide). The second biodegradable polymer may be a poly (D,L-lactide). For example, the implant may comprise a mixture of a first biodegradable polymer and a different second biodegradable polymer. One or more of the biodegradable polymers may have terminal acid groups. In certain implants, the matrix comprises a first biodegradable polymer having terminal acid groups, and a different second biodegradable polymer having terminal acid groups.

Release of a drug from an erodible polymer is the consequence of several mechanisms or combinations of mechanisms. Some of these mechanisms include desorption from the implant's surface, dissolution, diffusion through porous channels of the hydrated polymer and erosion. Erosion can be bulk or surface or a combination of both. As discussed herein, the matrix of the ocular implant may release drug at a rate effective to sustain release of an amount of siRNA for more than one week after implantation into an eye. In certain implants, therapeutic amounts of siRNA are released for no more than about 30-35 days after implantation. For example, an implant may comprise siRNA, and the matrix of the implant degrades at a rate effective to sustain release of a therapeutically effective amount of siRNA for about one month after being placed in an eye. As another example, the implant may comprise siRNA, and the matrix releases drug at a rate effective to sustain release of a therapeutically effective amount of siRNA for more than forty days, such as for about six months.

In one embodiment, the implant may be provided in the form of a rod or a filament produced by an extrusion process.

A implant formulation for the invention is siRNA 30%, R203S 45%, R202H 20%, cationic lipid or peptide 5%; or siRNA 20%, R203S 45%, R202H 10%, RG752S 20%, cationic lipid or peptide 5%. The range of concentrations of the constituents that can be used in the preferred implant formulation are siRNA 5 to 40%, R203S 10 to 60%, R202H 5 to 20%, RG752S 5 to 40%, cationic lipid or peptide 0 to 15%. The PLA/PLGA polymers are from the Resomer product line available from Evonik Industries, Germany, and include the listing in Table 1. R203S is a poly(D,L-lactide); and R752S is a 73:27 to 77:23 poly(D,L-lactide-co-glycolide).

TABLE 1

| Resomer | Monomer ratio | i.v. dL/g |
|---|---|---|
| RG502, | 50:50 poly (D,L-lactide-co-glycolide) | 0.2 |
| RG502H, | 50:50 poly (D,L-lactide-co-glycolide) | 0.2 |
| RG503, | 50:50 poly (D,L-lactide-co-glycolide) | 0.3 |
| RG504, | | 0.4 |
| RG505, | | 0.5 |
| RG506, | | 0.6 |
| RG752, | 75:25 poly (D,L lactide-co-glycolide) | 0.2 |
| RG755, | 75:25 poly(D,L lactide-co-glycolide) | 0.5 (40000) |
| RG756, | | 0.6 |
| RG858, | 85:15 poly (D,L-lactide-co-glycolide) | 1.0 |
| R202H, | poly (D,L-lactide) | 0.2 |
| R203 | poly (D,L-lactide) | 0.3 (40000) |
| R206. | poly (D,L-lactide); acid end | 0.6 |
| R104 | poly (D,L-lactide) | (3500) |

The release of the siRNA from the ocular implant comprising a biodegradable polymer matrix may include an initial burst of release followed by a gradual increase in the amount of the siRNA released, or the release may include an initial delay in release of the siRNA component followed by an increase in release. When the implant is substantially completely degraded, the percent of the siRNA that has been released is about one hundred.

It may be desirable to provide a relatively constant rate of release of the siRNA from the implant over the life of the implant. The release profile of the siRNA may include one or more linear portions and/or one or more non-linear portions. Preferably, the release rate is greater than zero once the implant has begun to degrade or erode.

The implants may be monolithic, i.e. having the active agent or agents homogenously distributed through the polymeric matrix, or encapsulated, where a reservoir of active agent is encapsulated by the polymeric matrix. Due to ease of manufacture, monolithic implants are usually preferred over encapsulated forms. However, the greater control afforded by the encapsulated, reservoir-type implant may be of benefit in some circumstances, where the therapeutic level of the siRNA falls within a narrow window. In addition, the complex, including the siRNA, may be distributed in a non-homogenous pattern in the matrix. For example, the implant may include a portion that has a greater concentration of the siRNA relative to a second portion of the implant.

The ocular implants disclosed herein may have a size of between about 5 μm and about 10 mm, or between about 10 μm and about 1 mm for administration with a needle, greater than 1 mm, or greater than 2 mm, such as 3 mm or up to 10 mm, for administration by surgical implantation. For needle-injected implants, the implants may have any appropriate length so long as the diameter of the implant permits the implant to move through a needle. For example, implants having a length of about 6 mm to about 7 mm have been injected into an eye. The implants administered by way of a needle should have a diameter that is less than the inner diameter of the needle. In certain implants, the diameter is less than about 500 μm. The vitreous chamber in humans is able to accommodate relatively large implants of varying geometries, having lengths of, for example, 1 to 10 mm. For example, humans have a vitreous volume of approximately 3.8 ml. The implant may be a cylindrical pellet (e.g., rod) with dimensions of about 2 mm×0.75 mm diameter. Or the implant may be a cylindrical pellet with a length of about 7 mm to about 10 mm, and a diameter of about 0.75 mm to about 1.5 mm.

The implants may also be at least somewhat flexible so as to facilitate both insertion of the implant in the eye, such as in the vitreous, and accommodation of the implant. The total weight of the implant is usually about 250-5000 μg, more preferably about 500-1000 μg. For example, an implant may be about 500 μg, or about 1000 μg. Thus, implants can be prepared where the center may be of one material and the surface may have one or more layers of the same or a different composition, where the layers may be cross-linked, or of a different molecular weight, different density or porosity, or the like. For example, where it is desirable to quickly release an initial bolus of drug, the center may be a polylactate coated with a polylactide-co-glycolide copolymer, so as to enhance the rate of initial degradation. Alternatively, the center may be polyvinyl alcohol coated with polylactate, so that upon degradation of the polylactate exterior the center would dissolve and be, rapidly washed out of the eye.

The implants may be of any geometry including fibers, sheets, films, microspheres, spheres, circular discs, plaques and the like. The upper limit for the implant size will be determined by factors such as toleration for the implant, size limitations on insertion, ease of handling, etc. Where sheets or films are employed, the sheets or films will be in the range of at least about 0.5 mm×0.5 mm, usually about 3-10 mm×5-10 mm with a thickness of about 0.1-1.0 mm for ease of handling. Where fibers are employed, the fiber diameter will generally be in the range of about 0.05 to 3 mm and the fiber length will generally be in the range of about 0.5-10 mm. Spheres may be in the range of about 0.5 .mu.m to 4 mm in diameter, with comparable volumes for other shaped particles.

The size and form of the implant can also be used to control the rate of release, period of treatment, and siRNA concentration at the site of implantation. Larger implants will deliver a proportionately larger dose, but depending on the surface to mass ratio, may have a slower release rate. The particular size and geometry of the implant are chosen to suit the site of implantation.

An implant of the present invention can be prepared using a hot-melt extrusion process. Hot-melt (or thermal) extrusion methods for preparing ocular implants are described in U.S. 2005/0244467, hereby incorporated by reference. See especially pages 9 and 10; and in U.S. 20100311808, hereby incorporated by reference. See especially Example 1 therein. An implant of the present invention may be produced using a hot-melt (or thermal) extrusion process by bringing the temperature of the siRNA/transfection agent/polymer powder blend to a temperature of about 25° C. to about 150° C., more preferably about 65° C. to about 130° C., and even more preferably about 60° C. to about 100° C. In certain embodiments, an implant of the present invention may be produced by bringing the temperature of the siRNA/transfection agent/polymer powder blend to a temperature of about 70° C. or about 80° C. In some embodiments the blend is maintained at the specified temperature for a time period of about 0 to 60 minutes, 0 to about 30 minutes, or about 5 to about 15 minutes to form a polymer/siRNA melt. For example, a time period may be about 5 minutes, about 10 minutes, about 15 minutes, about 30 minutes, about 45 minutes, or about 60 minutes. The implants are then extruded at a specified temperature, such as any of those temperatures given above. In addition, the implant may be coextruded so that a coating is formed over a core region during the manufacture of the implant. The transfection agent may, as used above, may be, for example, a peptide or cationic lipid.

The proportions of the siRNA complex, polymer, and any other modifiers present in an implant after manufacture may be empirically determined by formulating several implants with varying proportions. A USP approved method for dissolution or release test can be used to measure the rate of release (USP 23; NF 18 (1995) pp. 1790-1798). For example, using the infinite sink method, a weighed sample of the implant is added to a measured volume of a solution containing 0.9% NaCl in water, where the solution volume will be such that the siRNA complex concentration after release is less than 5% of saturation. The mixture is maintained at 37 .degree. C. and stirred slowly to maintain the implants in suspension. The appearance of the dissolved siRNA complex as a function of time may be followed by various methods known in the art, such as spectrophotometrically, HPLC, mass spectroscopy, etc. until the absorbance becomes constant or until greater than 90% of the drug has been released.

The cellular uptake of siRNA can be monitored by blending in a trace amount of fluorescein labeled siRNA and visualizing the localization of siRNA under fluorescence microscope. The gene silencing activities of siRNA released from the implants described here can be analyzed using a cultured mammalian cell assay.

In addition to the siRNA included in the ocular implants disclosed herein, the ocular implants may also include one or more additional ophthalmically acceptable therapeutic agents as described in U.S. patent application Ser. No. 10/837,260, incorporated entirely by reference. The ocular implants disclosed herein may also include effective amounts of buffering agents, preservatives and the like.

In certain implants, an implant comprising siRNA and a biodegradable polymer matrix is able to release or deliver an amount of siRNA between about 0.1 mg to about 0.5 mg for about 3-6 months after implantation into the eye. The implant may be configured as a rod or a wafer. A rod-shaped implant may be derived from filaments extruded from a 720 μm nozzle and cut into 1 mg size. Such implants may also be referred to as filamentous implants. A wafer-shaped implant may be a circular disc having a diameter of about 2.5 mm, a thickness of about 0.127 mm, and a weight of about 1 mg.

The present implants are configured to release an amount of siRNA effective to treat an ocular condition, such as by reducing at least one symptom of the ocular condition. More specifically, the implants may be used in a method to treat any angiogenic disorders like choroidal neovascularization associated with age related macular degeneration.

In one embodiment, an implant, such as the implants disclosed herein, is administered to a posterior segment of an eye of a human patient. In at least one embodiment, an implant is administered without accessing the subretinal space of the eye. For example, a method of treating a patient may include placing the implant directly into the posterior chamber of the eye. In other embodiments, a method of treating a patient may comprise administering an implant to the patient by at least one of intravitreal injection, subconjunctival injection, sub-tenon injections, retrobulbar injection, and suprachoroidal injection.

In addition, for dual therapy approaches to treating an ocular condition, the method may include one or more additional steps of administering additional therapeutic agents to the eye, such as by topically administering compositions containing said other therapeutic agent.

In certain implants, the implant comprises a therapeutic component, which consists essentially of a siRNA complex and a biodegradable polymer matrix. The biodegradable polymer matrix may consist essentially of PLA, PLGA, or a combination thereof. When placed in the eye, the implant releases about 10% to about 25% of the siRNA to provide a loading dose of the siRNA within about one day after placement in the eye. Subsequently, the implant releases about 1% to about 2% of the siRNA per day to provide a sustained therapeutic effect.

Other implants disclosed herein may be configured such that the amount of the siRNA that is released from the implant within two days of being placed in the eye is less than about 95% of the total amount of the siRNA in the implant. In certain implants, 95% of the siRNA is not released until after about one week of being placed in an eye. In certain implants, about 50% of the siRNA is released within about one day of placement in the eye, and about 2% is released for about 1 month after being placed in the eye. In other implants, about 50% of the siRNA is released within about one day of placement in the eye, and about 1% is released for about 2 months after being placed in the eye.

In certain embodiments, the present invention is directed to an ocular implant comprising a small interfering RNA (siRNA) complexed with a transfection agent, the transfection agent selected from the group consisting of cationic lipids and cell penetration peptides, wherein said complex is associated with a biocompatible polymer, wherein said biocompatible polymer comprises a polymeric matrix configured to release said complex into the eye of a patient at therapeutic levels for a time sufficient to treat an ocular condition or disease. In certain embodiments, the polymer or polymer matrix is configured to release the complex into the eye of a patient for at least about one day or more. In other embodiments, the polymer or polymer matrix is configured to release the complex into the eye of a patient for at least about one week. In these embodiments the short cell penetration peptide may be selected from the group consisting of polylysines, polyarginines, Pep-1, and MPG. The cationic lipid can be any of Cetyl trimethylammonium bromide, Cetylpyridinium chloride, Polyethoxylated tallow amine, Benzalkonium chloride, Benzethonium chloride, 1,2-distearoyl-sn-glycero-3-ethyl phosphocholine chloride, Dimethyldioctadecylammonium bromide, and 1,2-dioleoyl-3-trimethylammonium-propane chloride.

The present invention is also directed to an improved method for increasing the duration of the release of siRNA from an ocular implant, the improvement comprising increasing the loading of siRNA by complexing said siRNA with a transfection agent selected from the group consisting of cationic lipids and cell penetration peptides, and associating said complex with a biocompatible polymer. In this method, the cell penetration peptide is selected from the group consisting of polylysines, polyarginines (e.g., R9), Pep-1, and MPG. Cationic lipids for use in this method include, but are not limited to, Cetyl trimethylammonium bromide, Cetylpyridinium chloride, Polyethoxylated tallow amine, Benzalkonium chloride and Benzethonium chloride.

Also within the scope of the invention is a biodegradable ocular implant, comprising a small interfering RNA (siRNA), a transfection agent, and a biodegradable polymer, wherein the siRNA is complexed with the transfection agent, and wherein said complex is associated with the biodegradable polymer, the transfection agent selected from the group consisting of peptides and cationic lipids. Exemplary peptides include polylysines, polyarginines, Pep-1, and MPG. Exemplary cationic lipids include Cetyltrimethylammonium bromide, Cetylpyridinium chloride, Polyethoxylated tallow amine, Benzalkonium chloride, Benzethonium chloride, 1,2-distearoyl-sn-glycero-3-ethyl phosphocholine chloride, Dimethyldioctadecylammonium bromide, and 1,2-dioleoyl-3-trimethylammonium-propane chloride. The biodegradable polymer can comprise a poly (D,L-lactide-co-glycolide) (PLGA) copolymer or a poly (D,L-lactide) (PLA) polymer or both a PLGA copolymer and PLA polymer. In more specific embodiments the implant may consist of or consist essentially of about 14% by weight siRNA, about 81% by weight biodegradable polymer, and about 5% by weight transfection agent, wherein the transfection agent is a cationic lipid or peptide, wherein the implant provides sustained release of an siRNA for at least 24 hours after placement in an eye.

The present invention also encompasses biodegradable implants comprising microRNAs (miRNAs) complexed with a transfection agent selected from the group consisting of cationic lipids and short cell penetration peptides (peptides between about 5 and about 50 amino acids in length), wherein said complex is associated with a biocompatible polymer or polymer matrix, configured to release said complex into the eye of a patient at therapeutic levels for a time sufficient to treat an ocular condition.

The present invention also encompasses biodegradable implants comprising microRNAs (miRNAs) complexed with a transfection agent selected from the group consisting of cationic lipids and short cell penetration peptides (peptides between about 5 and about 50 amino acids in length), wherein said complex is associated with a biocompatible polymer or polymer matrix, configured to release an amount of said complex into the eye of a patient for at least about one day.

The present invention is also directed to an ocular implant comprising a small interfering RNA (siRNA) complexed with a transfection agent, according to any of the embodiments described above, wherein the transfection agent is a cell penetration peptide and the implant is made by the process comprising the steps of:
  (a) mixing a cell penetration peptide with an siRNA in aqueous solution to form a complex, followed by
  (b) lyophilizing the solution into a dry powder, followed by
  (c) blending the dry powder of (b) with a dry biodegradable polymer powder, the polymer selected from the group consisting of a polylactide (PLA) and a poly (lactide-co-glycolide) (PLGA), followed by
  (d) heating the blend of (c) for a time and at a temperature sufficient to form a semi-molten material, followed by
  (e) extruding the material of (d) at a temperature to form a solid filamentous implant.

The present invention is also directed to an ocular implant comprising a small interfering RNA (siRNA) complexed with a transfection agent, according to any of the embodiments described above, wherein the transfection agent is a cationic lipid and the implant is made by the process comprising the steps of:
  (a) dissolving the cationic lipid in ethanol, followed by
  (b) mixing the ethanol solution of (a) with an aqueous solution of siRNA, followed by
  (c) lyophilizing the mixture of (b) into a dry powder, followed by
  (d) blending the dry powder of (c) with a dry biodegradable polymer powder, the polymer selected from the group consisting of a polylactide (PLA) and a poly (lactide-co-glycolide) (PLGA), followed by
  (e) heating the blend of (d) for a time and at a temperature sufficient to form a semi-molten material, followed by
  (f) extruding the material of (e) at a temperature to form a solid filamentous implant.

DEFINITIONS

The following terms as used herein have the following meanings:

An implant that provides "Sustained release" for a specified period of time is one that continually or continuously releases an amount of an active agent, such as an siRNA, for the specified period of time.

Unless otherwise specified, the terms "complexed with," "complex," and "complexes" refer to a group of two or more components joined together by non-covalent bonds only, formed upon admixture of the components under conditions permitting the formation of such bonds. Non-covalent bonds can include electrostatic or ionic bonds.

"Therapeutic level" refers to the amount of drug or pharmaceutically active agent, such as the amount of siRNA, that will reduce, lessen, alleviate, or reverse a symptom associated with or accompanying a pathological condition of the eye.

An "ocular implant" is a biocompatible composition of matter that is sized, structured, or otherwise configured to be placed in an eye of a living mammalian subject. In some embodiments the implant is sized and structured for insertion, placement, or injection into an ocular region of the eye of a human subject.

The "glass transition temperature" refers to the softening temperature of a biodegradable polymer or polymer combination, such as a PLGA copolymer, PLA polymer, or a PLGA/PLA combination. The "glass transition temperature" is the transition temperature above which the noncrystalline polymer has enough thermal energy for long segments of each polymer chain to move randomly. At a temperature higher than the glass transition temperature, the polymer molecules become mobile, forming a "fluidized medium" or "semi-molten material." The temperature used to form the fluidized medium or semi-molten material should be sufficient to soften the polymer for hot melt extrusion but below the temperature that might otherwise promote substantial degradation of the active agent, e.g., siRNA or miRNA associated with the polymer.

As used herein, an "ocular region" or "ocular site" refers generally to any area of the eyeball, including the anterior and posterior segment of the eye, and which generally includes, but is not limited to, any functional (e.g., for vision) or structural tissues found in the eyeball, or tissues or cellular layers that partly or completely line the interior or exterior of the eyeball. Specific examples of areas of the eyeball in an ocular region include the anterior chamber, the posterior chamber, the vitreous cavity, the choroid, the suprachoroidal space, the conjunctiva, the subconjunctival space, the episcleral space, the intracorneal space, the epicorneal space, the sclera, the pars plana, surgically-induced avascular regions, the macula, and the retina.

The term "therapeutically effective amount" as used herein, refers to the level or amount of agent needed to treat an ocular condition, or reduce or prevent ocular injury or damage without causing significant negative or adverse side effects to the eye or a region of the eye.

The term "treat", "treating", or "treatment" as used herein, refers to reduction or resolution or prevention of an ocular condition, ocular injury or damage, or to promote healing of injured or damaged ocular tissue. More specifically, the term "treating" refers to reducing or lessening a symptom associated with or accompanying a pathological condition in an eye. The individual treated with any of an implant of the present invention can be a human or non-human mammal.

As used herein, "a polylysine peptide" is considered to be an amino acid chain of between about 3 and about 50 contiguous lysines. In certain embodiments, the polylysine peptide is 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 contiguous lysines in length.

As used herein "a polyarginine peptide" is considered to be an amino acid chain of between about 3 and about 50 contiguous arginines. In certain embodiments, the polyarginine peptide is 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 contiguous arginines in length.

"R9" is a polyarginine peptide consisting of 9 contiguous arginines.

As used herein "a peptide" is considered to be a short polymer of between about 3 and about 50 contiguous amino acids in length, wherein the amino acids are linked by peptide bonds. In certain embodiments, a peptide is 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 contiguous amino acids in length.

As used herein, a "cell penetration peptide" is a peptide that facilitates cellular uptake of another molecular component, such as an siRNA or miRNA, which is associated with the peptide through non-covalent interactions. Cell penetration peptides are typically polycationic or amphipathic.

A "short cell penetration peptide" is a cell penetration peptide of between about 3 and about 50 contiguous amino acids in length.

A "cationic lipid" is an amphiphilic molecule composed of a hydrophobic end(s) (e.g., one or two fatty acid side chains (saturated or unsaturated)) and a hydrophilic end (e.g., an amino or ammonium head group). The hydrophobic and hydrophilic ends are generally attached to one another via linker. Cationic lipids form complexes with nucleic acids, such as siRNAs and miRNAs through electrostatic interactions.

The term "biodegradable polymer" refers to a polymer or polymers which degrade in vivo, and wherein erosion of the polymer or polymers over time occurs concurrent with or subsequent to release of the therapeutic agent. Specifically, hydrogels such as methylcellulose which act to release drug through polymer swelling are specifically excluded from the term "biodegradable polymer". The terms "biodegradable" and "bioerodible" are equivalent and are used interchangeably herein. A biodegradable polymer may be a homopolymer, a copolymer, or a polymer comprising more than two different polymeric units.

As used herein, "associated with" means mixed with or dispersed within. Unless otherwise specified, "associations" and "associated with" as used herein refer to non-covalent interactions.

The term "siRNA" refers to RNA duplexes (i.e., double stranded RNAs) about 18 to about 30 base pairs in length that are capable of triggering cleavage of a complementary mRNA via the RNA interference (RNAi) pathway. More preferably, the siRNA is 19 to 25 base pairs in length, and even more preferably 19 to 23 base pairs in length. An siRNA may have blunt ends or 1 to 3 base overhangs at one or both ends of the siRNA. In one embodiment, an siRNA consists of separate, non-covalently linked sense and antisense strands that are each 21 nucleotides in length and that base-pair with one another to form a perfectly complementary 19-base pair duplex with a 2 nucleotide overhang at each end.

The term "biocompatible" means compatible with living tissue or a living system by not being toxic, injurious, or physiologically reactive and not causing an immunological reaction.

"Ocular implant" means a device or element that is structured, sized, or otherwise configured to be placed "in an eye" of a living mammal, including the subconjunctival space. Ocular implants are generally biocompatible with physiological conditions of an eye and do not cause adverse side effects. Ocular implants may be placed in an eye without disrupting vision of the eye.

The following U.S. Patent Application Publications are hereby incorporated by reference:

U.S. Patent Application Publication 2009/0258924, hereby incorporated by reference, discloses biocompatible sustained-release intraocular drug delivery systems comprising an siRNA, a polymeric component, and a release modifying excipient, such as a fatty alcohol, glycol, or polysaccharide.

U.S. Patent Application Publication 2009/0226531, hereby incorporated by reference, discloses nanoparticles encapsulating siRNA that may be placed in the eye to treat or reduce the occurrence of one or more ocular conditions.

U.S. Patent Application Publication 2008/0107694, hereby incorporated by reference, discloses a biocompatible sustained release intraocular drug delivery system comprising a protein or polynucleotide therapeutic agent, a polymeric carrier, and a long chain fatty alcohol release modifier.

The following examples are intended to illustrate the present invention.

EXAMPLE

TABLE 2

Cationic lipids used in cellular uptake enabling PLGA implants of siRNA

| | |
|---|---|
| 18:0 EPC (Cl Salt) | 1,2-distearoyl-sn-glycero-3-ethyl phosphocholine (chloride salt) |
| 18:0 DDAB | Dimethyldioctadecylammonium (Bromide Salt) |
| 18:1 TAP | 1,2-dioleoyl-3-trimethylammonium-propane (chloride salt) |
| transfection reagent (DOTAP:DOPE) (1:1 w/w) | 1,2-dioleoyl-sn-glycero-3-phosphoethanolamine |
| | 1,2-dioleoyl-3-trimethylammonium-propane (chloride salt) |

A cationic lipid or transfection reagent containing cationic lipids (see Table 2) was dissolved in ethanol, and mixed with siRNA in water to form a complex (aqueous blending). The mixture was then lyophilized into a dry powder and then blended with a PLGA polymer (also in powder form). The powder blend was then formed into an implant (Table 3) using a hot-melt extrusion process. As a comparison, a non-cationic lipid (DSPE-PEG (2000) amine: 1,2-distearoyl-sn-glycero-3-phosphoethanolamine-N-[amino(polyethylene glycol)-2000] (ammonium salt)) was used instead of a cationic lipid (J-7 in Table 2).

In another group, the same lipids were directly mixed with siRNA as well as PLGA polymer via powder blending to generate the implants with the same compositions (Table 3).

TABLE 3

Formulations of implants containing cationic or functionalized PEG lipid

| Sample # | Formulation | Blending of siRNA and lipid |
|---|---|---|
| J-5 | 14% siRNA, 5% transfection reagent (DOTAP:DOPE), 81% RG752S | aqueous |
| J-6 | 14% siRNA, 5% 18:1 TAP, 81% RG752S | aqueous |
| J-8 | 14% siRNA, 5% 18:0 DDAB, 81% RG752S | aqueous |
| J-9 | 14% siRNA, 5% 18:0 EPC, 81% RG752S | aqueous |
| J-7 | 14% siRNA, 5% DSPE-PEG(2000) amine, 81% RG752S | aqueous |
| J-1 | 14% siRNA, 5% 18:0 EPC, 81% RG752S | powder |
| J-2 | 14% siRNA, 5% DSPE-PEG(2000) amine, 81% RG752S | powder |
| J-3 | 14% siRNA, 5% 18:0 DDAB, 81% RG752S | powder |
| J-4 | 14% siRNA, 5% transfection reagent (DOTAP:DOPE), 81% RG752S | powder |

Alternatively, a cell penetrating peptide selected from the following was co-dissolved with siRNA in water and lyophilized into dry powder.

Peptide MPG:
(SEQ ID NO: 2)
H-GALFLGFLGAAGSTMGAWSQPKSKRKV-OH

Peptide pep-1:
(SEQ ID NO: 1)
H-KETWWETWWTEWSQPKKKRKV-OH

The above dry mixture was then mixed with PLGA powder and implants (Table 4) were made with a hot-melt extrusion process.

TABLE 4

Formulation of implants containing cell-penetrating peptide

| | |
|---|---|
| J-10 | 14% siRNA, 5% peptide MPG, 81% RG752S |
| J-11 | 14% siRNA, 5% peptide (pep-1), 81% RG752S |

The day one release study was done in phosphate buffered saline (PBS) solution (release medium) (pH 7.4, 0.01 M) at 37° C. in a shaking water bath at 50 rpm. After 24 hrs, the solution containing the released free siRNA was analyzed by HPLC. The amount of siRNA released from the implant, as a percentage of the total siRNA initially present in the implant, is shown for each implant in FIG. 1.

The results showed that when either cationic lipid or peptide was blended with anionic siRNA in aqueous solution, the burst release of free siRNA from the implant was low, possibly due to the formation of a complex between the siRNA and the cationic lipid or peptide. siRNA in complex with cationic lipid or peptide could either be released, but not detected by the HLPC method, or remain in the implant for a slower release. The latter was possible since the siRNA-lipid or siRNA-peptide complex would be more neutral in charge, and thus more chemically compatible with PLGA polymeric matrix. On the other hand, when the cationic lipid and siRNA were mixed together in dry form, as in the case of powder blending, even with the same implant composition, the burst release of free siRNA was significantly higher, possible suggesting that, with the powder blending process, no siRNA/transfection reagent complexes are formed either at the blending or hot-melt extrusion stage. The complexation between anionic siRNA and cationic lipid or peptide was likely mediated by charge-charge interaction, as the one with anionic lipid (J2 and J7) showed high burst release of free siRNA, suggesting there was no siRNA-lipid complex.

Further examination of the released siRNA-cationic lipid or siRNA-cationic peptide complex from the implant would reveal their release profile and cellular uptake activities.

The present invention is not to be limited in scope by the exemplified embodiments, which are only intended as illustrations of specific aspects of the invention. Various modifications of the invention, in addition to those disclosed herein, will be apparent to those skilled in the art by a careful reading of the specification, including the claims, as originally filed. It is intended that all such modifications will fall within the scope of the appended claims.

What is claimed is:

1. A method for increasing the duration of the release of siRNA from an ocular implant, the improvement comprising increasing the loading of siRNA by complexing said siRNA with a transfection agent selected from the group consisting of cationic lipids and cell penetration peptides, and associating said complex with a biocompatible polymer wherein said ocular implant is configured to release said complex into the eye of a patient for a time sufficient to treat an ocular condition or disease.

2. The method of claim 1, wherein said cell penetration peptide is selected from the group consisting of polylysines, polyarginines, Pep-1 (SEQ ID NO:1), and MPG (SEQ ID NO:2).

3. The method of claim 1 wherein said cationic lipid is selected from the group consisting of Cetyl trimethyl ammonium, Cetyl peridinium chloride, Polyethoxylated tallow amine, Benzalkonium chloride and Benzethonium chloride.

* * * * *

SEQUENCE LISTING

```
<160> NUMBER OF SEQ ID NOS: 2

<210> SEQ ID NO 1
<211> LENGTH: 21
<212> TYPE: PRT
<213> ORGANISM: Artificial Sequence
<220> FEATURE:
<223> OTHER INFORMATION: Synthetic peptide Pep-1

<400> SEQUENCE: 1

Lys Glu Thr Trp Trp Glu Thr Trp Trp Thr Glu Trp Ser Gln Pro Lys
1               5                   10                  15

Lys Lys Arg Lys Val
            20

<210> SEQ ID NO 2
<211> LENGTH: 27
<212> TYPE: PRT
<213> ORGANISM: Artificial Sequence
<220> FEATURE:
<223> OTHER INFORMATION: Synthetic peptide MPG

<400> SEQUENCE: 2

Gly Ala Leu Phe Leu Gly Phe Leu Gly Ala Ala Gly Ser Thr Met Gly
1               5                   10                  15

Ala Trp Ser Gln Pro Lys Ser Lys Arg Lys Val
            20                  25
```